United States Patent [19]
Torii

[11] Patent Number: 6,030,079
[45] Date of Patent: Feb. 29, 2000

[54] METHOD FOR ANALYZING AN IMAGE OF A FUNDUS, AND AN APPARATUS FOR EXECUTING THAT METHOD

[75] Inventor: Miwako Torii, Aichi, Japan

[73] Assignee: Nidek Co., Ltd., Aichi, Japan

[21] Appl. No.: 09/197,638

[22] Filed: Nov. 23, 1998

[30] Foreign Application Priority Data

Nov. 21, 1997 [JP] Japan .................................. 9-337998

[51] Int. Cl.[7] ...................................................... A61B 3/10
[52] U.S. Cl. ........................................................... 351/205
[58] Field of Search ................................. 351/205, 206, 351/221, 211, 213, 222; 600/398, 401; 356/388, 390, 392, 393

[56] References Cited

U.S. PATENT DOCUMENTS

| | | | |
|---|---|---|---|
| 4,824,238 | 4/1989 | Feldman et al. | 351/206 |
| 4,991,584 | 2/1991 | Kobayashi et al. | 351/211 |
| 5,315,329 | 5/1994 | McAdams | 351/206 |

FOREIGN PATENT DOCUMENTS

| | | | |
|---|---|---|---|
| 0 846 439 A1 | 6/1998 | European Pat. Off. | A61B 3/14 |
| 7-136121 | 5/1995 | Japan | A61B 3/12 |
| 8-567 | 1/1996 | Japan | A61B 3/14 |

*Primary Examiner*—George Manuel
*Attorney, Agent, or Firm*—Sughrue, Mion, Zinn, Macpeak & Seas, PLLC

[57] ABSTRACT

A method for analyzing an image of a fundus to analyze an optic disc on the basis of the image of the fundus includes: a first step of producing a disc line and a cup line on a same planar image, on the basis of the image of the fundus; a second step of obtaining a longest distance in a predetermined direction of each of a disc region determined by the produced disc line and a cup region determined by the produced cup line; and a third step of computing a C/D ratio on the basis of longest distances of the regions in the predetermined direction.

10 Claims, 8 Drawing Sheets

FIG. 9  < COMPUTATION ROUTINE OF VERTICAL C/D RATIO >

METHOD FOR ANALYZING AN IMAGE OF A FUNDUS, AND AN APPARATUS FOR EXECUTING THAT METHOD

BACKGROUND OF THE INVENTION

1. Field of the Invention

The present invention relates to a method for analyzing an image of a fundus to detect and analyze the optic disc on the basis of the image of the fundus, and an apparatus for executing that method, and particularly to a method and an apparatus which are suitable for computation of optic disc parameters.

2. Detailed Description of the Related Art

Glaucoma is known as a disease of the visual function. In the examination of glaucoma, it is said that the observation of patient's optic disc on the basis of an image of the fundus is important. In recent years, it has become possible to quantitatively measure the optic disc due to progress in the technology of image analysis.

As one of parameters indicating the size of the optic disc cupping in an image analysis, used is a C/D ration which is a distance ratio between a margin of the optic disc cupping (the optic disc cupping being referred to as a cup) and a margin of the optic disc (the optic disc being referred to as a disc). Usually, the C/D ratio is separately computed as a vertical C/D ratio in the vertical direction and a horizontal C/D ratio in the horizontal direction.

These ratios are computed by the following method. As shown in FIG. 11, the vertical C/D ratio is obtained as a ratio of the average of the sizes of the disc margin and that of the sizes of the cup margin on five meridians of 70° to 110° centered at the center of gravity of the disc and at intervals of 10°. The horizontal C/D ratio is obtained as a ratio of the average of the sizes of the disc margin and that of the sizes of the cup margin on five meridians of 340° to 20° centered at the center of gravity of the disc and at intervals of 10°.

However, in the case where, as shown in FIG. 12, there is a cup margin portion 100 in which the degree of edema of the optic disc or coloboma of the optic nerve fiber is relatively low in the,vertical direction, or there is a small coloboma portion 101 of the optic nerve fiber, the vertical and horizontal C/D ratios computed in the above-mentioned method may be largely different from the finding of the oculist in clinic. Further, in the case where the cup is eccentric with respect to the center of gravity of the disc, the C/D ratio computed in the above-mentioned method may be different from the finding of the oculist, thereby producing a problem in that the computation is not sufficient.

SUMMARY OF THE INVENTION

In view of the above-described problems of the conventional art, a technical tack of the present invention is to provide a method for analyzing an image of a fundus which can adequately compute a C/D ratio close the finding of the oculist in clinic, and an apparatus for performing the method.

To overcome the above-described problems, the present invention is characterized by the following-features.

(1) A method for analyzing an image of a fundus to analyze an optic disc on the basis of the image of the fundus includes:

a first step of producing a disc line and a cup line on a same planar image, on the basis of the image of the fundus;

a second step of obtaining a longest distance in a predetermined direction of each of a disc region determined by the produced disc line and a cup region determined by the produced cup line; and a third step of computing a C/D ratio on the basis of longest distances of the regions in the predetermined direction.

(2) A method for analyzing an image of a fundus according to (1), wherein the predetermined direction includes a vertical direction and a horizontal direction, in the second step, the longest distances in the vertical and horizontal directions of each of the disc region and the cup region are obtained, and in the third step, a vertical C/D ratio is computed on the basis of the longest distances in the vertical direction of the regions, and a horizontal C/D ratio is computed on the basis of the longest distances in the horizontal direction of the regions.

(3) A method for analyzing an image of a fundus according to (1), wherein, in the second step, maximum and minimum points in the predetermined direction are detected for each of the disc region and the cup region, the longest distance of the disc region in the predetermined direction is obtained on the basis of the detected maximum and minimum points of the disc region, and the longest distance of the cup region in the predetermined direction is obtained on the basis of the detected maximum and minimum points of the cup region.

(4) A method for analyzing an image of a fundus according to (3), wherein, in the second step, a position of the center of gravity of one of the disc region and the cup region is obtained, a scan line in the predetermined direction being perpendicular to a reference line passing through the position of the center of gravity is subjected to scanning in a direction perpendicular to the predetermined direction, so as to detect maximum and minimum values of intersections of the scan line and the disc line, and maximum and minimum values of intersections of the scan line and the cup line, the longest distance in the predetermined direction of the disc region is obtained on the basis of the detected maximum and minimum values of intersections of the scan line and the disc line, and the longest distance in the predetermined direction of the cup region is obtained on the basis of the detected maximum and minimum values of intersections of the scan line and the cup line.

(5) In a method for analyzing an image of a fundus according to (4), wherein, in the second step, when an intersection of the scan line and the disc line is not further detected, the scanning of the scan line is ended.

(6) A method for analyzing an image of a fundus according to (1), wherein, in the first step, the cup line is produced on the basis of a stereoscopic fundus image.

(7) An apparatus for analyzing an image of a fundus to analyze an optic disc on the basis of the image of the fundus includes:

an image data inputting unit for inputting data of the image of the fundus;

an image producing unit for producing a disc line and a cup line in a same planar image on the basis of the image of the fundus which is input through the image data inputting unit;

a storage unit for storing a program computing a C/D ratio on the basis of the disc line and the cup line which are produced by the image producing unit, the program including: a step of obtaining a longest distance in a predetermined direction of each of a disc region determined by the produced disc line and a cup region determined by the produced cup line; and a step of computing the C/D ratio based on the longest distances in the predetermined direction of the regions; and a program executing unit for executing the program.

(8) An apparatus for analyzing an image of a fundus according to (7), further includes a displaying unit for displaying a result computed by executing the program.

(9) An apparatus for analyzing an image of a fundus according to (7), further includes an outputting unit for outputting a result computed by executing the program.

(10) An apparatus for analyzing an image of a fundus according to (7), further includes a storing unit for storing a result computed by executing the program.

DETAILED DESCRIPTION OF THE PREFERRED EMBODIMENT

Figure 1:
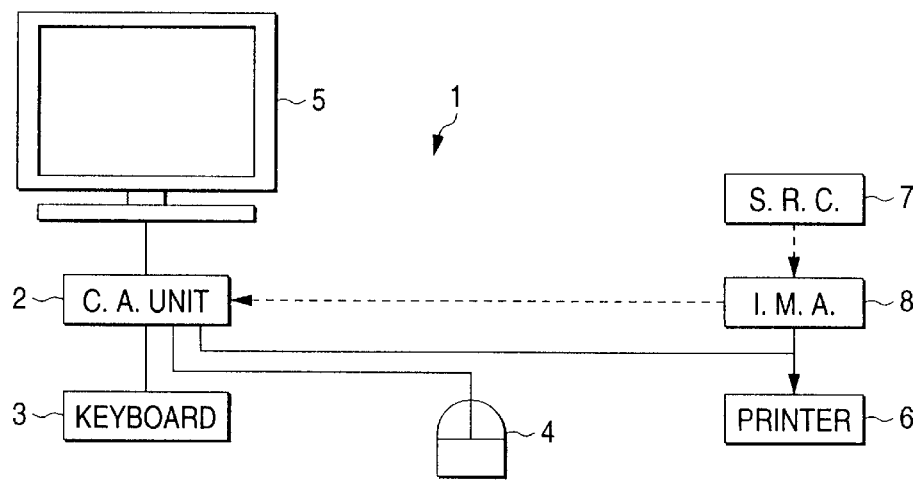
FIG. 1 is a schematic block diagram of the apparatus in accordance with an embodiment.
Figure 2:
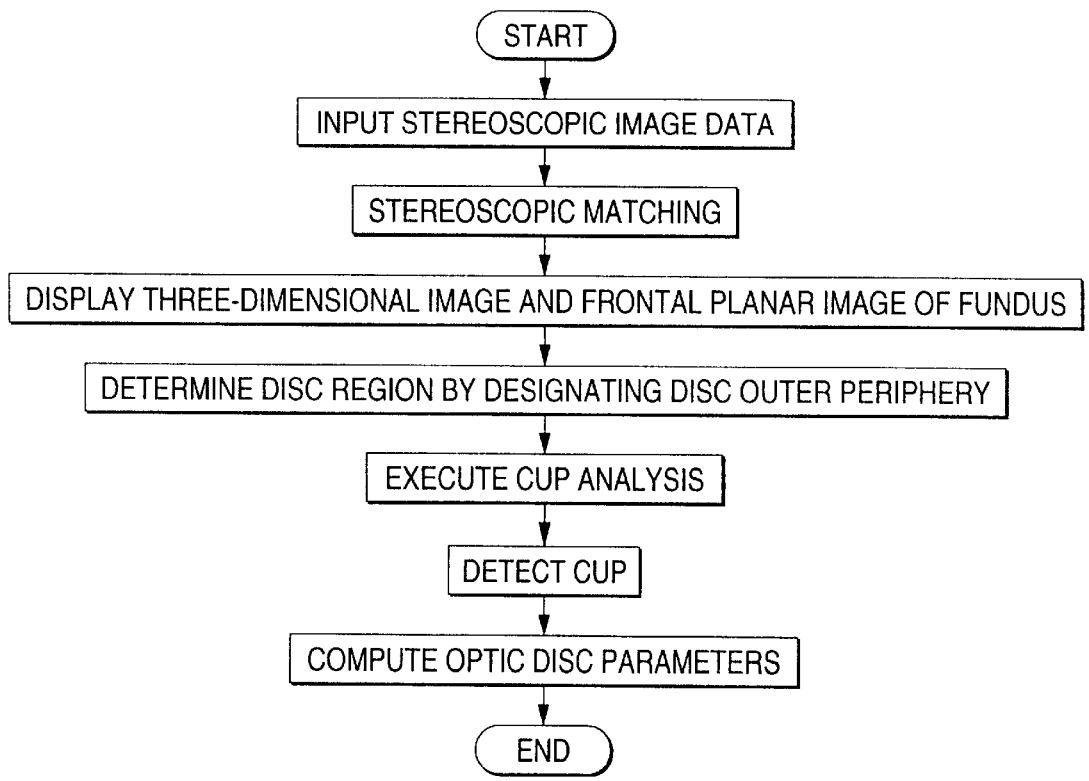
FIG. 2 is a diagram illustrating a flowchart of the overall analysis of an image of the fundus of the eye.
Figure 3:
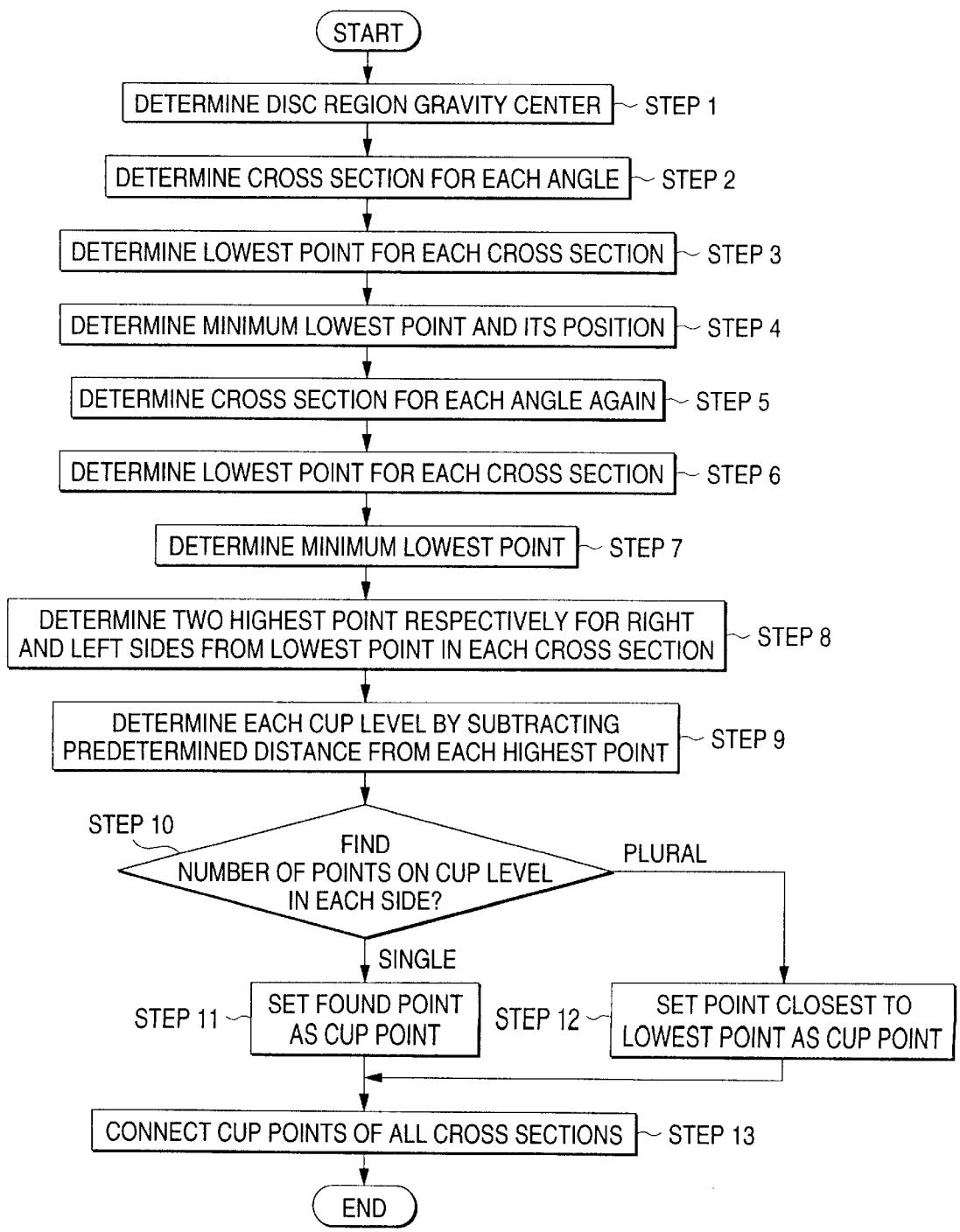
FIG. 3 is a diagram illustrating a flowchart for detecting the cup.

Referring now to the drawings, a description will be given of an embodiment of the present invention. FIG. 1 is a schematic block diagram of an apparatus in accordance with the embodiment. An analyzing apparatus 1 is comprised of a computing and analyzing unit 2, a keyboard 3 and a mouse 4 which constitute a designation input section, a display 5 for displaying an image of a fundus, the results of analysis, and the like, and a printer 6. A commercially available personal computer can be used as the analyzing unit 2. Also, commercially available ones can be used as the other component parts. Reference numeral 7 denotes a stereoscopic retinal (fundus) camera, wherein a bundle of illumination light rays reflected from the fundus is separated into two bundle of rays by a bifurcating (two-hole) diaphragm to obtain a pair of right and left stereoscopic images. The stereoscopic image of the fundus photographed by the stereoscopic retinal (fundus) camera 7 is converted into image data by an image reading apparatus 8, and is inputted to the computing and analyzing unit 2. As the stereoscopic retinal (fundus) camera 7, it is possible to use a type in which image of the fundus is photographed on a transparency film, or a type in which an image on the fundus is photographed by a CCD camera. In the case of the latter type, after the image of the fundus is recorded in an image recording means as a still picture, the image of the fundus is inputted into the computing and analyzing unit 2 directly or via a recording medium such as a floppy disk. <Computation of Disc Margin and Cup Margin>

Next, a description will be given of the analysis of an image of the fundus by means of the computing and analyzing unit 2 (see FIGS. 2 to 5). First, a pair of stereoscopic image data of the fundus photographed by the stereoscopic retinal (fundus) camera 7 is inputted into the computing and analyzing unit 2. The computing and analyzing unit 2 incorporates correction based on a parallax, a magnification of image formation, a distortion due to aberrations and the like into the inputted stereoscopic image data, subjects the corrected stereoscopic image data to stereoscopic matching, and obtains three-dimensional data of the fundus on the basis of the same. As the stereoscopic matching, it is possible to use an apparatus disclosed in Japanese Patent Application Laid-Open No. 8-567 (Title of the Invention: Fundus Oculi Measuring Instrument).

Subsequently, an outer peripheral line of the disc is designated. On the basis of the three-dimensional data of the fundus, a bird's-eye view (or a triangular net) showing a three-dimensional image (configuration) of the fundus and a front view showing a planar image (frontal, planar configuration) of the fundus are displayed on the display 5, and the operator designates a disc region in the displayed three-dimensional image or planar image of the fundus. The designation of the disc region is effected as follows. Since a pointer for designating an outer peripheral line of the disc is displayed in the three-dimensional image and the planar image on the display 5, the pointer is moved and then the mouse 4 is clicked to designate a multiplicity of (preferably, 10 or more) points on the outer peripheral line of the disc.

After the designation of the outer peripheral line of the disc, the operator instructs the execution of cup analysis processing to the computing and analyzing unit 2. The computing and analyzing unit 2 first effects the detection of the cup. The detection of the cup is effected in accordance with the flowchart shown in FIG. 3.

The designated points are connected by a cubic spline curve in such a manner as to form a smooth line, and that line is depicted in such a manner as to be superposed on the planar image on the display 5. By depicting the designated points by the spline curve, it is possible to determine the outer peripheral line of the disc in a shape which approximates a real one very closely. In addition, it is possible to cope with even the outer periphery of the disc which has a distorted shape. The computing and analyzing unit 2 sets its inner side as the disc region, and determines the position of its center of gravity (Step 1). The position of the center of gravity serves as a tentative central position, on the basis of which the position of a lowest point within the disc region is determined.

The computing and analyzing unit 2 determines a cross Asection of the disc for each predetermined detection angle (e.g., for each 1 degree) by using as the center the position of the center of gravity determined in Step 1 (Step 2), and determines a lowest point (a deepest point) for each cross section of the disc (Step 3). A minimum lowest point as well as its position in the disc region are determined among the lowest points for the respective cross sections of the disc determined in Step 3 (Step 4). By using as the center the position of the minimum lowest point determined in Step 4, the cross section of the disc is determined again for each predetermined detection angle (e.g., for each 1 degree) (Step 5). Further, lowest points in the respective cross sections of the disc determined in Step 5 are determined (Step 6), and a minimum lowest point is determined among the lowest points determined in Step 6 (Step 7). This minimum lowest point determined in Step 7 approximates a true lowest point within the disc region.

Figure 4:
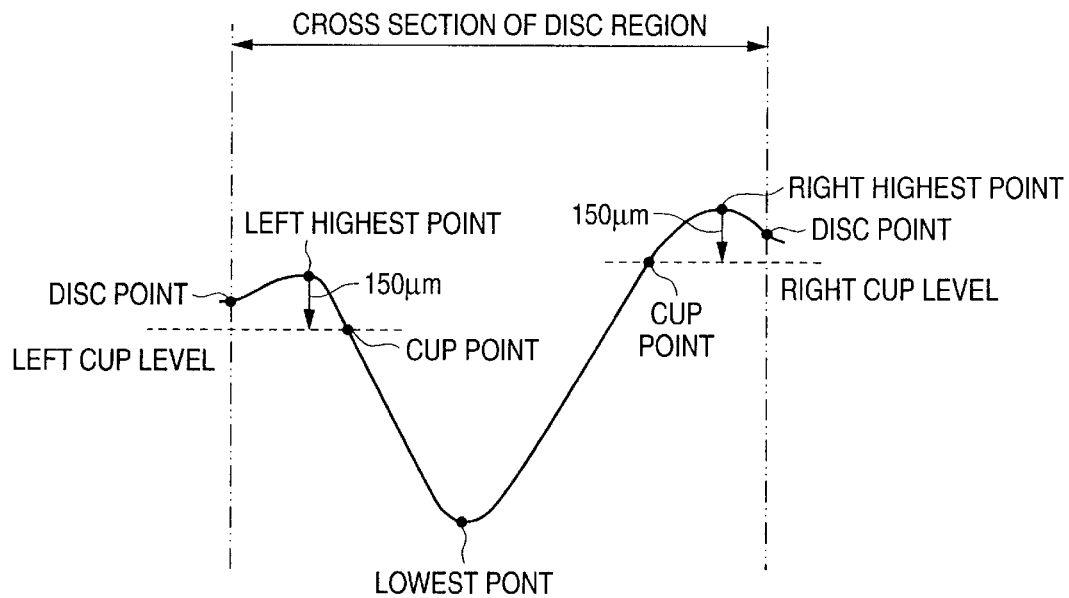
FIG. 4 is a diagram explaining the steps for determining the cup level in a cross section of the disc.
Figure 5:
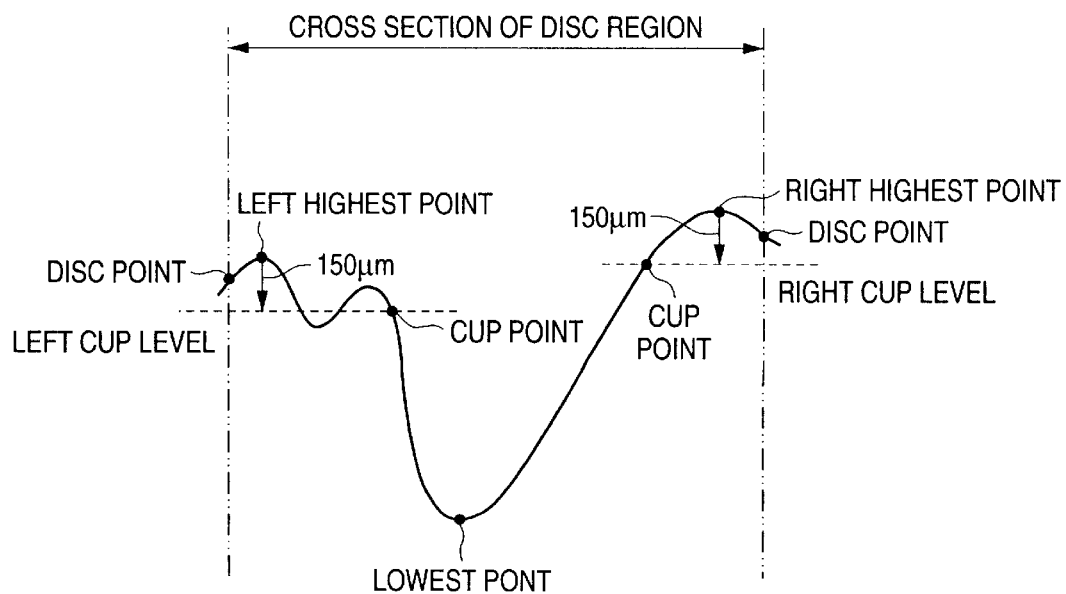
FIG. 5 is a diagram explaining a method for determining cup points when there are a plurality of points which reached the cup level.

Two highest points in both directions between the lowest point in each cross section of the disc determined in Step 6 and each of the disc point on either side (either end of the cross section of the disc) are respectively determined (Step 8), and the level which is lower from each of the determined highest points by a predetermined distance (e.g., 150 μm) is set as each cup level (Step 9, see FIG. 4).

Points on the cup level are searched in each cross section of the disc left and right directions from the lowest point determined in Step 6, the number of points which reached the cup level are found (Step 10), and if the number of points which reached the cup level is one for each of the left and right directions from the lowest point determined in Step 6, that point is set as the cup point (Step 11). When there are a plurality of points which reached the cup level, a point which is closest to the lowest point determined in Step 6 is set as the cup point (Step 12, see FIG. 5). The cup points determined for the respective cross sections are connected to obtain the cup margin (Step 13).

Through the above-described method, even if the plane of the disc is inclined, it is possible to detect the cup margin accurately and improve reproducibility as well.

<Computation of Disc Parameters>

Figure 6:
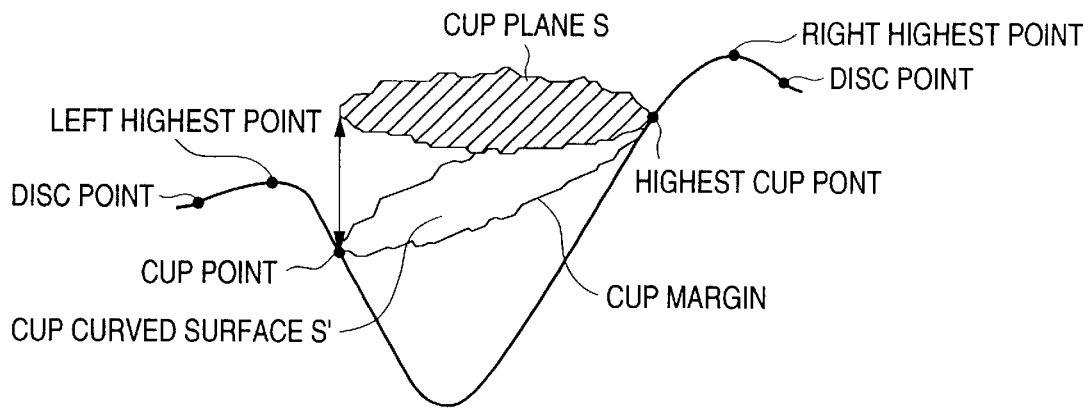
FIG. 6 is a diagram explaining a method for obtaining a cup plane S.

Subsequently, the computing and analyzing unit 2 computes various parameters of the optic disc on the basis of the computed data of the cup. In the computation of the parameters of the optic disc, as shown in FIG. 6, a cup plane S is obtained by taking a highest point of the cup margin as a reference position and by projecting a curved surface S' of the cup defined by the cup margin onto a horizontal plane (reference plane) including the reference position. The outer peripheral line of this cup plane S is used in computation as the cup margin data.

Figure 7:
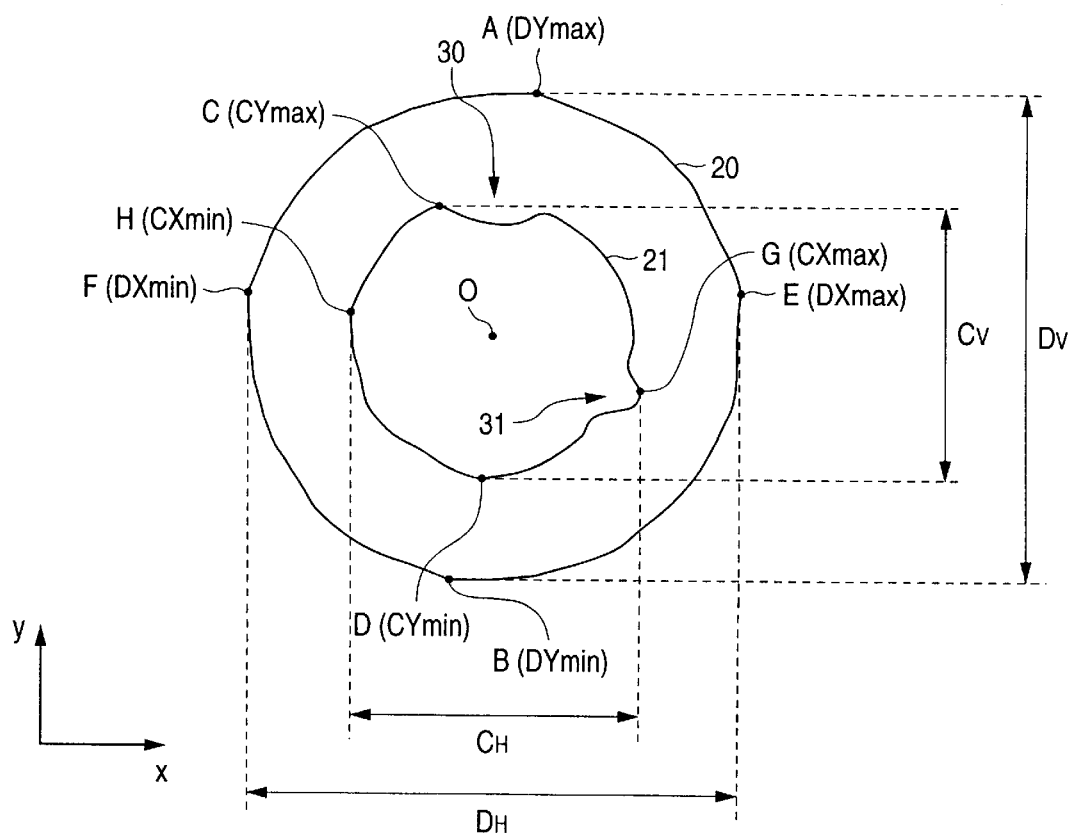
FIG. 7 is a diagram showing an example of a planar image of a disc line and a cup line.
Figure 8:
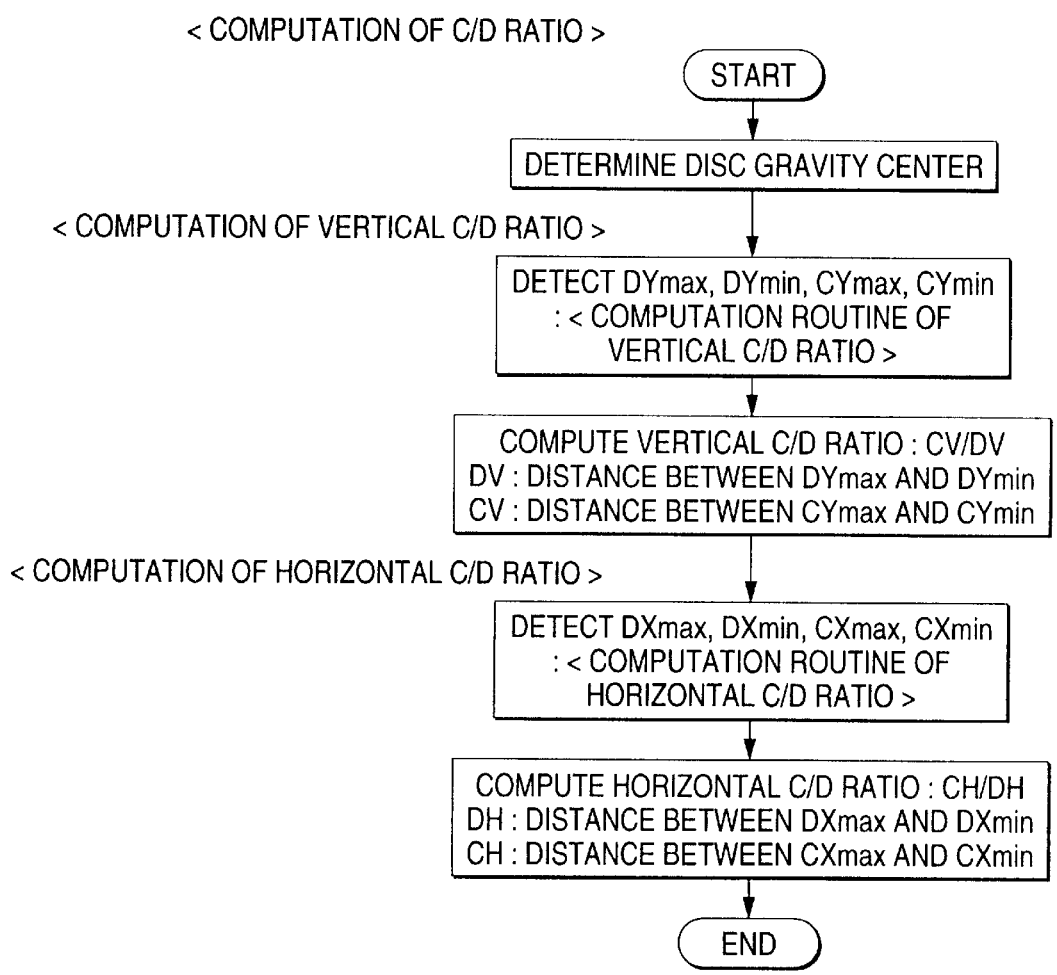
FIGS. 8 to 10 are diagrams illustrating a flowchart of the computation of a C/D ratio.
Figure 9:
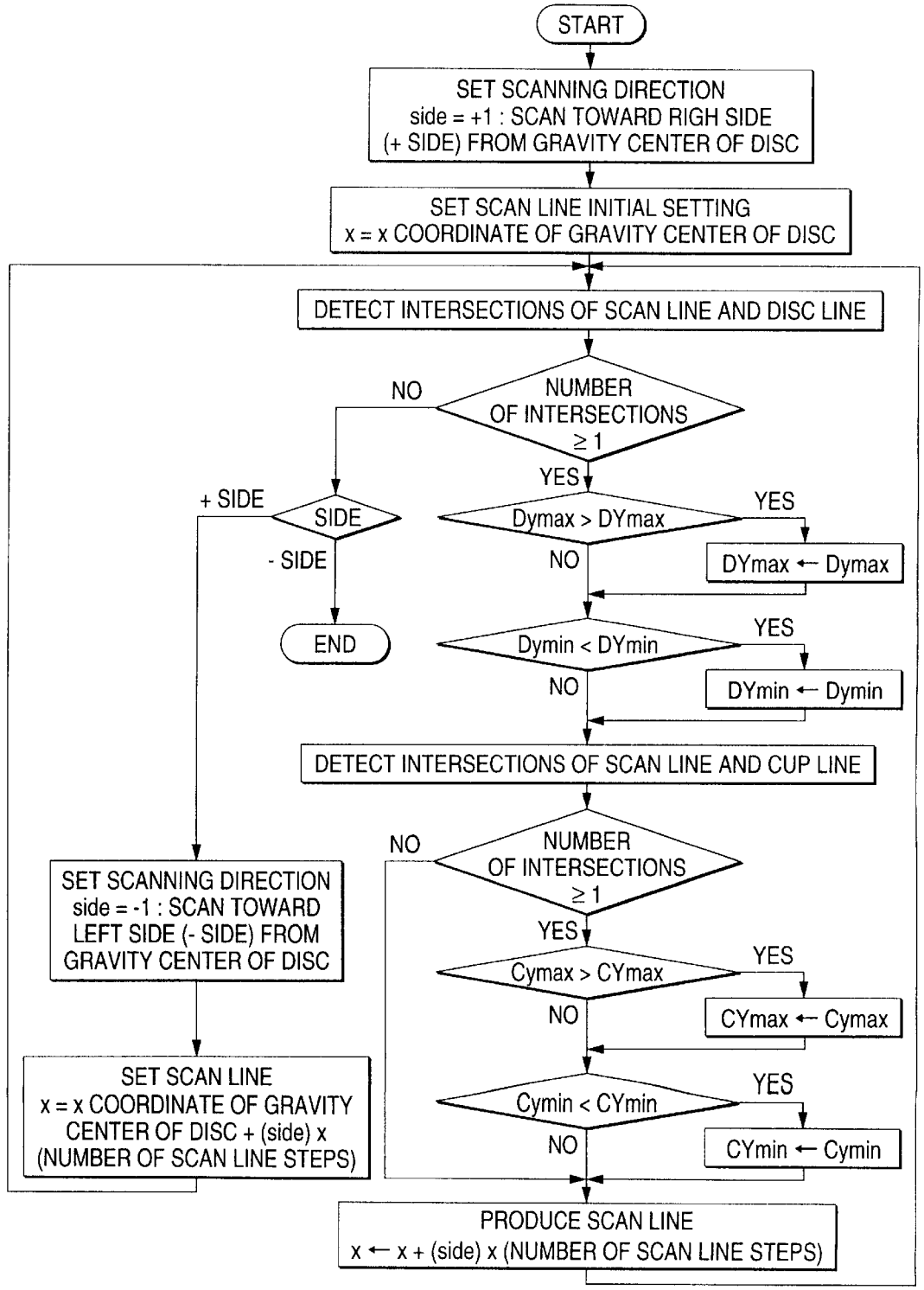
Figure 10:
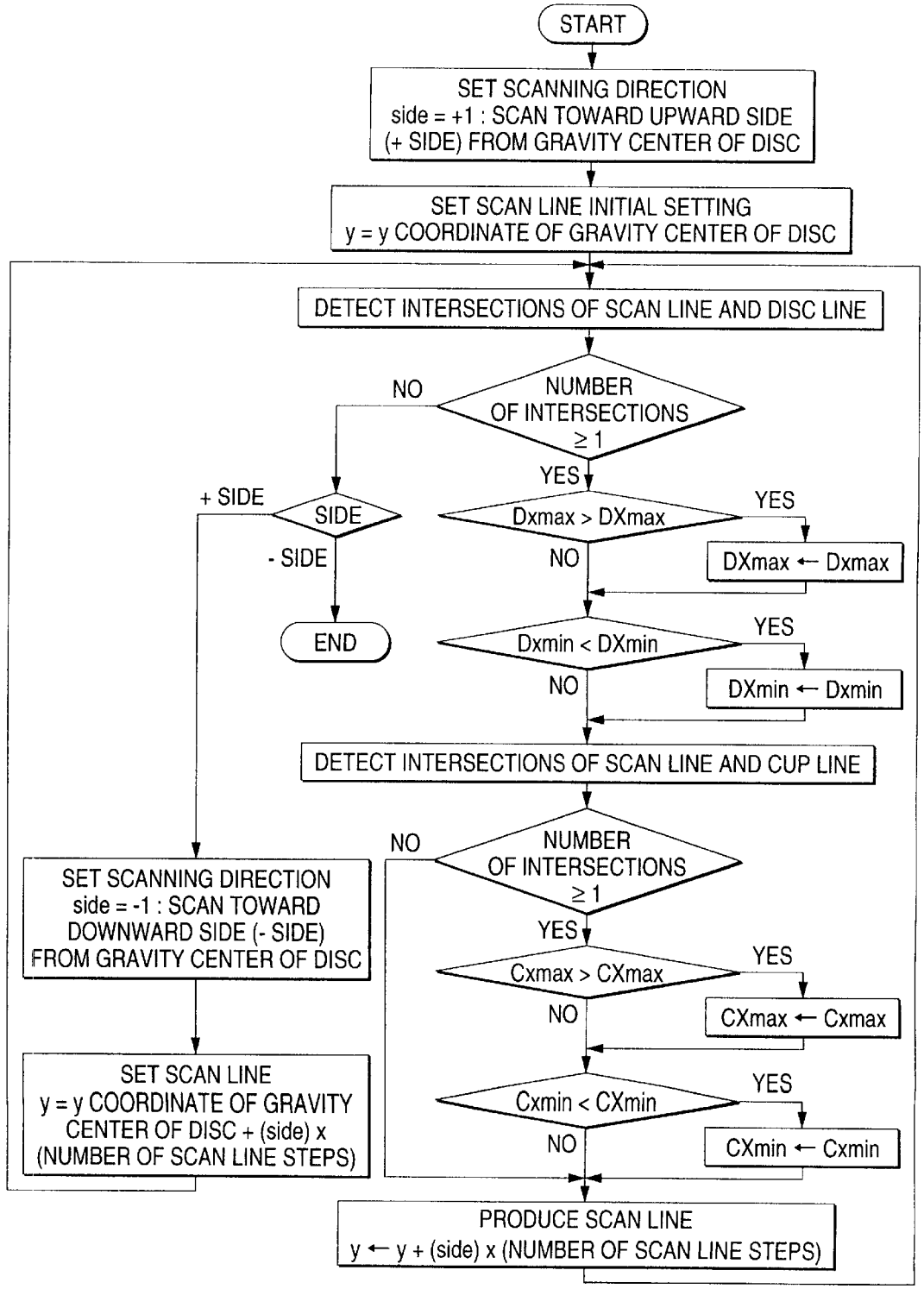
Figure 11:
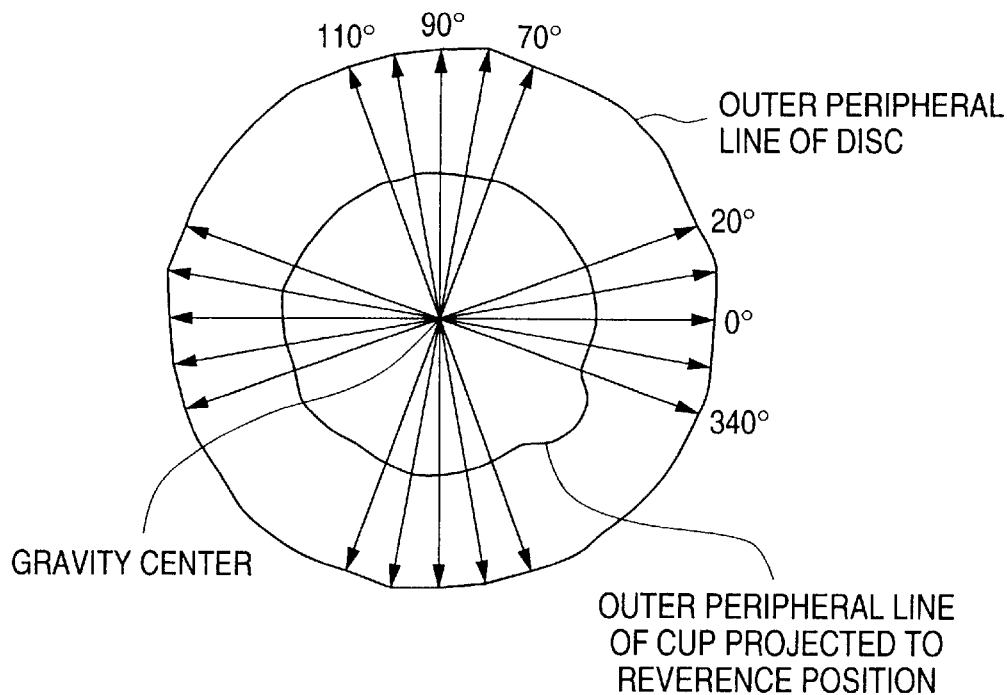
FIGS. 11 and 12 are diagrams illustrating a method of computing a C/D ratio in the related art.
Figure 12:
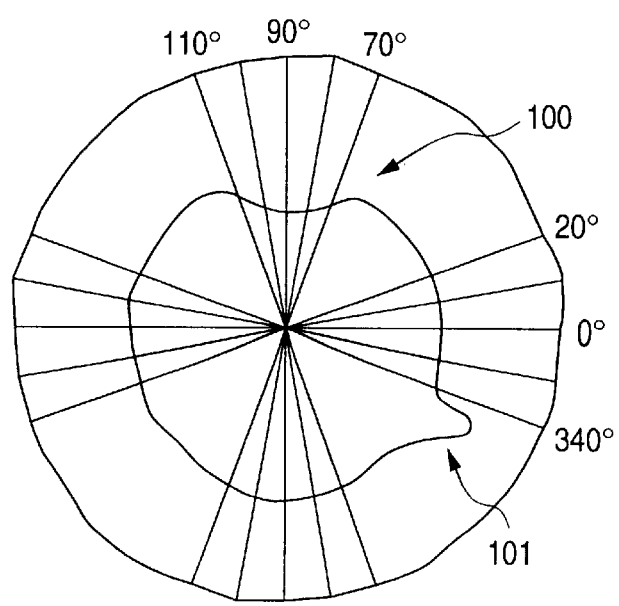

A description will be given of the computation of the C/D ratio which is one of the disc parameters. In accordance with the data of the cup margin and the outer peripheral line of the disc thus computed, a planar image as shown in FIG. 7 which has a disc line 20 and a cup line 21 is produced. Based on the planar image, the vertical and horizontal C/D ratios are obtained in the following manner (see the flowcharts of FIGS. 8, 9 and 10).

(A) Computation of vertical C/D ratio

The position O of the center of gravity is obtained from the disc line 20 (or the cup line 21). A scan line in the vertical direction based on the x coordinate of the position O of the center of gravity is produced as initial setting. First, the scanning is sequentially performed toward the right side (+ side) of the x coordinate and at a predetermined step. When one or more intersections of the scan line produced at the reference position and the disc line 20 are detected (at the first time, two or more intersections are detected), the maximum value Dymax and the minimum value Dymin of the y coordinates of the intersections are obtained (in the first scanning, DYmax and DYmin are set. In addition, when the number of the intersections is one, the y coordinate of the intersection is obtained in both Dymax and Dymin). When an intersection with the disc line 20 is detected in the next second scanning, the maximum value Dymax and the minimum value Dymin of the y coordinate of the intersection obtained in this case are respectively compared with the maximum value DYmax and the minimum value DYmin of the y coordinates which are previously obtained. As a result of the comparison of the maximum values Dymax and DYmax, the lager value is set as the new maximum value DYmax, and, as a result of the comparison of the minimum values Dymin and DYmin, the smaller value is set as the new minimum value DYmin. Thereafter, the maximum value DYmax and the minimum value DYmin are obtained while sequentially performing scanning toward the right side (+ side) of the x coordinate.

When one or more intersections of the scan line and the cup line 21 are detected, similarly, the maximum value Cymax and the minimum value Cymin of the y coordinates of the intersections are obtained, and the values are respectively compared with the maximum value CYmax and the minimum value CYmin of the y coordinates which are previously obtained, so that the new maximum value CYmax and the new minimum value CYmin are obtained. The cup line 21 and the disc line 20 are drawn in different image arrangements, and hence intersections with the scan line can be distinguishedly obtained.

When one or more intersections of the scan line and the disc line 20 are not detected in the scanning toward the right side (+ side) of the x coordinate, the scanning is then sequentially performed toward the left side (− side) of the x coordinate with respect to the position O of the center of gravity and at a predetermined step. When one or more intersections of the scan line, and the disc line 20 and the cup line 21 are detected, similarly, Dymax and Dymin, and Cymax and Cymin are obtained, and the values are respectively compared with DYmax and DYmin, and CYmax and CYmin which are previously obtained, so that new DYmax and DYmin, and CYmax and CYmin are obtained. When one or more intersections of the scan line and the disc line 20 are not detected in the scanning toward the left side (− side) of the x coordinate, the scanning in the vertical direction is ended, and the final DYmax and DYmin, and CYmax and CYmin are obtained. In the example shown in FIG. 7, DYmax=the point A and DYmin=the point B, each of which is the region defined by the disc line 20, CYmax= the point C and CYmin=the point D, each of which is the region defined by the cup line 21 are obtained.

From the distance DV in the vertical direction obtained from the maximum value DYmax and the minimum value DYmin of the disc line 20 thus obtained, and the distance CV in the vertical direction obtained from the maximum value CYmax and the minimum value CYmin of the cup line 21, the vertical C/D ratio which is a ratio of the distances is computed.

(B) Computation of horizontal C/D ratio

A similar process is performed on the x coordinate while the scanning direction of the scan line in the computation of the vertical C/D ratio is changed to the horizontal direction. Namely, the scan line in the horizontal direction based on the y coordinate of the position O of the center of gravity is initially set, and the scanning is sequentially performed toward the upward side (+ side) of the y coordinate. When one or more intersections of the scan line, and the disc line 20 and the cup line 21 are detected, the maximum value Dxmax and the minimum value Dxmin of the x coordinates of intersections of the scan line and the disc line 20, and the maximum value Cxmax and the minimum value Cxmin of intersections with the scan line and the cup line 21 are obtained, and the values are respectively compared with DXmax and DXmin, and CXmax and CXmin which are previously obtained, so that new DXmax and DXmin, and CXmax and CXmin are obtained. When one or more intersections of the scan line and the disc line 20 are not detected, the same process is performed while the scanning is then sequentially performed toward the downward side (− side) of the y coordinate with respect to the position O of the center of gravity, and the final DXmax and DXmin, and CXmax and CXmin are obtained. In the example of FIG. 7, the point E=DXmax, the point F=DXmin, the point G=CXmax, and the point H=CXmin are obtained. The horizontal C/D ratio is computed by the horizontal direction CH between the points G and H, and the horizontal direction DH between the points E and F.

In the image processing described above, a reference is set in the region of the disc line 20, scanning is performed vertically and horizontally with starting from the reference, and, when an intersection with the disc line 20 is not further detected, the scanning is ended. As compared with the case where the points A to H are obtained by scanning over the whole of the image region, therefore, it is possible to prevent the image processing from being performed in a superfluous region, to thereby shorten the process time.

In the detection of the points A to H, in place of performing the scanning in both the vertical and horizontal directions as described above, the x and y coordinates of intersections of the scan line in one of the directions and the lines 20 and 21 may be obtained at one time, and the maximum and minimum values of the coordinates may be then obtained.

According to the method described above, also in the case where, as shown in FIG. 7, there is a cup margin portion 30 in which the degree of coloboma of the optic nerve fiber in the vertical direction is relatively low, or a cup margin portion 31 of small coloboma of the optic nerve fiber, or a cup being eccentric with respect to the center of gravity of the disc, a C/D ratio which is close to the finding based on the fundus observation can be computed with reflecting various conditions in the periphery of the optic disc.

As the parameters of the optic disc, in addition to the C/D ratio, the area (Cup Area) of the plane within the cup margin, the area ratio (C/D Area Ratio) between the cup and the disc, the depth of the cup (Max Cup Depth), the volume of the cup (Cup Volume), and the like are computed. The computed disc parameters are displayed on a display device 5, stored in a hard disk device or the like, and output to a floppy disk or the like, or printed out.

As described above, according to the invention, it is possible to compute an adequate C/D ratio with high reliability, with reflecting various conditions in the periphery of the optic disc.

The foregoing description of the preferred embodiments of the invention has been presented for the purpose of illustration and description only. It is not intended to be exhaustive or to limit the invention to the precise form disclosed, and modifications and variations are possible in light of and within the scope of the invention. The preferred embodiments were chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and equivalents thereof.

What is claimed is:

1. A method for analyzing an image of a fundus to analyze an optic disc on the basis of the image of the fundus, the method comprising:

a first step of producing a disc line and a cup line on a same planar image, on the basis of the-image of the fundus;

a second step of obtaining a longest distance in a predetermined direction of each of a disc region determined by the produced disc line and a cup region determined by the produced cup line; and a third step of computing a C/D ratio on the basis of longest distances of the regions in the predetermined direction.

2. A method for analyzing an image of a fundus according to claim 1, wherein the predetermined direction includes a vertical direction and a horizontal direction, in the second step, the longest distances in the vertical and horizontal directions of each of the disc region and the cup region are obtained, and in the third step, a vertical C/D ratio is computed on the basis of the longest distances in the vertical direction of the regions, and a horizontal C/D ratio is computed on the basis of the longest distances in the horizontal direction of the regions.

3. A method for analyzing an image of a fundus according to claim 1, wherein, in the second step, maximum and minimum points in the predetermined direction are detected for each of the disc region and the cup region, the longest distance of the disc region in the predetermined direction is obtained on the basis of the detected maximum and minimum points of the disc region, and the longest distance of the cup region in the predetermined direction is obtained on the basis of the detected maximum and minimum points of the cup region.

4. A method for analyzing an image of a fundus according to claim 3, wherein, in the second step, a position of the center of gravity of one of the disc region and the cup region is obtained, a scan line in the predetermined direction being perpendicular to a reference line passing through the position of the center of gravity is subjected to scanning in a direction perpendicular to the predetermined direction, so as to detect maximum and minimum values of intersections of the scan line and the disc line, and maximum and minimum values of intersections of the scan line and the cup line, the longest distance in the predetermined direction of the disc region is obtained on the basis of the detected maximum and minimum values of intersections of the scan line and the disc line, and the longest distance in the predetermined direction of the cup region is obtained on the basis of the detected maximum and minimum values of intersections of the scan line and the cup line.

5. A method for analyzing an image of a fundus according to claim 4, wherein, in the second step, when an intersection of the scan line and the disc line is not further detected, the scanning of the scan line is ended.

6. A method for analyzing an image of a fundus according to claim 1, wherein, in the first step, the cup line is produced on the basis of a stereoscopic fundus image.

7. An apparatus for analyzing an image of a fundus to analyze an optic disc on the basis of the image of the fundus, the apparatus comprising:

image data inputting means for inputting data of the image of the fundus;

image producing means for producing a disc line and a cup line in a same planar image on the basis of the image of the fundus which is input through the image data inputting means;

storage means for storing a program computing a C/D ratio on the basis of the disc line and the cup line which are produced by the image producing means, the program comprising: a step of obtaining a longest distance in a predetermined direction of each of a disc region determined by the produced disc line and a cup region determined by the produced cup line; and a step of computing the C/D ratio based on the longest distances in the predetermined direction of the regions; and program executing means for executing the program.

8. An apparatus for analyzing an image of a fundus according to claim 7, further comprising displaying means for displaying a result computed by executing the program.

9. An apparatus for analyzing an image of a fundus according to claim 7, further comprising outputting means for outputting a result computed by executing the program.

10. An apparatus for analyzing an image of a fundus according to claim 7, further comprising storing means for storing a result computed by executing the program.

* * * * *